United States Patent
Stoianovici et al.

(10) Patent No.: US 7,477,927 B2
(45) Date of Patent: Jan. 13, 2009

(54) SYSTEM AND METHOD FOR LASER BASED COMPUTED TOMOGRAPHY AND MAGNETIC RESONANCE REGISTRATION

(75) Inventors: Daniel Stoianovici, Baltimore, MD (US); Alexandru Patriciu, Baltimore, MD (US); Louis Kavoussi, Lotherville, MD (US); Gabor Fichtinger, Kensington, MD (US)

(73) Assignee: The Johns Hopkins University, Baltimore, MD (US)

( * ) Notice: Subject to any disclaimer, the term of this patent is extended or adjusted under 35 U.S.C. 154(b) by 1311 days.

(21) Appl. No.: 10/367,953

(22) Filed: Feb. 19, 2003

(65) Prior Publication Data

US 2004/0162486 A1    Aug. 19, 2004

Related U.S. Application Data

(60) Provisional application No. 60/357,451, filed on Feb. 15, 2002.

(51) Int. Cl.
*A61B 5/05* (2006.01)

(52) U.S. Cl. .................. 600/427; 600/424; 600/429

(58) Field of Classification Search ............... 600/427, 600/424; 378/62, 98; 382/130; 606/130
See application file for complete search history.

(56) References Cited

U.S. PATENT DOCUMENTS

| | | | |
|---|---|---|---|
| 4,068,763 A | 1/1978 | Fltecher et al. |
| 4,098,001 A | 7/1978 | Watson |
| 4,149,278 A | 4/1979 | Frosch et al. |
| 4,355,469 A | 10/1982 | Nevins et al. |
| 4,409,736 A | 10/1983 | Seltzer |
| 4,477,975 A | 10/1984 | De Fazio et al. |
| 4,501,522 A | 2/1985 | Causer et al. |
| 4,537,557 A | 8/1985 | Whitney |
| 4,556,203 A | 12/1985 | Rourke et al. |
| 4,666,361 A | 5/1987 | Kitabatake et al. |
| 4,970,448 A | 11/1990 | Torii et al. |
| 5,078,140 A | 1/1992 | Kwoh |
| 5,207,114 A | 5/1993 | Salisbury et al. |
| 5,305,653 A | 4/1994 | Ohtani et al. |
| 5,397,323 A | 3/1995 | Taylor et al. |

(Continued)

OTHER PUBLICATIONS

Image Guidance of Therapy, M.A. Viergever, IEEE Transactions on Medical Imaging, editorial for special issue on image guidance of therapy, vol. 17, No. 5, Oct. 1998, pp. 669-671.*

(Continued)

*Primary Examiner*—Brian L. Casler
*Assistant Examiner*—John F Ramirez
(74) *Attorney, Agent, or Firm*—Arent Fox LLP

(57) ABSTRACT

A method and system for laser based instrument registration. The system includes an operating table coupled with a robot holding an instrument, and CT scanner. The CT scanner has first and second laser markers. The method includes moving the robot to align the instrument in a first position wherein a tip of the instrument is disposed within a first laser plane created by the first laser marker. Then, the robot moves the instrument to a second position wherein the entire instrument is disposed within the first laser plane. Coordinate data of the robot in the second position is obtained. Image data of a first slice is obtained from the CT scanner. The registration data is calculated based on the coordinate data and the image data.

29 Claims, 3 Drawing Sheets

U.S. PATENT DOCUMENTS

| | | | |
|---|---|---|---|
| 5,515,478 A | | 5/1996 | Wang |
| 5,531,520 A | * | 7/1996 | Grimson et al. ............. 382/131 |
| 5,572,999 A | | 11/1996 | Funda et al. |
| 5,630,431 A | | 5/1997 | Taylor |
| 5,647,554 A | | 7/1997 | Ikegami et al. |
| 5,772,580 A | | 6/1998 | Utsui et al. |
| 5,792,135 A | | 8/1998 | Madhani et al. |
| 5,806,518 A | | 9/1998 | Mittelstadt |
| 5,817,084 A | | 10/1998 | Jensen |
| 5,876,325 A | | 3/1999 | Mizuno et al. |
| 5,907,664 A | | 5/1999 | Wang et al. |
| 6,047,610 A | | 4/2000 | Stocco et al. |
| 6,055,449 A | * | 4/2000 | Navab ........................ 600/427 |
| 6,105,454 A | | 8/2000 | Bacchi et al. |
| 6,246,200 B1 | | 6/2001 | Blumenkranz et al. |
| 6,267,022 B1 | | 7/2001 | Suzuki |
| 6,408,224 B1 | | 6/2002 | Okamoto et al. |
| 6,558,107 B1 | | 5/2003 | Okuno |
| 6,675,671 B1 | | 1/2004 | Jokiel et al. |
| 6,889,119 B2 | | 5/2005 | Riff et al. |
| 7,225,012 B1 | * | 5/2007 | Susil et al. .................. 600/414 |
| 2002/0038855 A1 | * | 4/2002 | Hwang .................. 250/559.29 |
| 2003/0000535 A1 | * | 1/2003 | Galloway et al. ........... 128/898 |
| 2003/0097060 A1 | * | 5/2003 | Yanof et al. ............. 600/424 |
| 2005/0033315 A1 | * | 2/2005 | Hankins .................... 606/129 |

OTHER PUBLICATIONS

M.H. Loser et al.; "Visual Servoing for Automatic and Uncalibrated Percutaneous Procedures"; Proc. SPIE vol. 3976; pp. 270-281; Medical Imaging 2000: Image Display and Visualization; Seong K. Mun; Ed., published Apr. 2000: 12 pages.

N. Navab et al.; "Visual Servoing for Automatic and Uncablibrated Needle Placement for Percutaneous Procedures", Proc. Of IEEE Conf. On Computer Vision and Pattern Recognition, Jun. 13-15, 2000: Hilton Head Island, South Carolina, USA, 8 pages.

* cited by examiner

SYSTEM AND METHOD FOR LASER BASED COMPUTED TOMOGRAPHY AND MAGNETIC RESONANCE REGISTRATION

CROSS REFERENCE TO RELATED APPLICATION

This application claims priority to provisional patent application No. 60/357,451, entitled LASER BASED CT AND MR REGISTRATION, filed on Feb. 15, 2002, the contents of which are incorporated herein by reference.

BACKGROUND OF THE INVENTION

1. Field of the Invention

The present invention relates to robotic devices used in computer-assisted surgery. In particular, the invention relates to systems and methods for computer assisted laser-based instrument registration with a computed tomography (CT) and magnetic resonance (MR) imaging system.

2. Description of the Related Art

Minimally invasive and noninvasive procedures for surgery are gaining increased popularity mainly due to reduced trauma to patients and improved recovery time. One of the main problems encountered in minimally invasive procedures is, in contrast to open surgical procedures, a dramatic reduction in the surgeon's visual ability. Accordingly, radiological, ultrasonic, and magnetic resonance imaging techniques are employed to map anatomical geometry during intra-operative procedures.

Computed tomography (CT) guided percutaneous procedures are becoming increasingly popular in radiological interventions. CT guided interventions have been facilitated by the development of the CT fluoroscopy (CTF) imaging systems, which are a new generation of CT-scanners that allow for fluoro-imaging of a CT slice. Using the real-time cross-section image, the radiologist can manually orient and insert a procedure needle towards the target, provided that the skin entry point and the target are located in the current fluoro-slice. Even though the procedure is fast and precise in experienced hands, the major limitation of CTF is the relatively high radiation exposure to patient and physician. In order to make the real time adjustments in needle trajectory the physician's hand is often disposed in or near the scanning plane. Such hand exposure has been theoretically and empirically determined to be approximately 2 mGy per procedure [see, Nawfel R D, Judy P F, Silverman S G; Hooton S, Tuncali K, Adams D F: Patient and personnel exposure during at fluoroscopy-guided interventional procedures. Radiology (2000) 216:180-184]. If an annual dose limit of 500 mSv for the hands were presumed, a physician would be limited to performing only four CTF procedures per year.

A number of procedural techniques, shields, and passive needle holders have been proposed to reduce radiation exposure during such operations. Robotic systems have been investigated for eliminating radiation exposure and simultaneously increasing accuracy in radiological intervention.

One system using CT-fluoroscopy was reported by Loser and Navab, in Loser M H, Navab N: A new robotic system for visually controlled percutaneous interventions under CT fluoroscopy, MICCAI 1999, Lecture Notes in Computer Science, Springer-Verlag (2000) 1935:887-896. This system used a visual-servoing algorithm to orient the procedure needle based on fluoro-CT images. The approach demonstrated good targeting accuracy by using the procedure needle as a marker, without additional registration hardware. Even though the radiation exposure of the surgeon supervising the procedure from the control room is virtually zero, the patient is still being exposed to radiation during the robot's image-based servo orientation.

Susil et al. reported a registration method using a localization device (a modified Brown-Roberts-Wells frame) attached to the end-effector for the robot, which was further modified by Masamune. See Susil R C, Anderson J, Taylor R H: A Single Image Registration Method for CT Guided Interventions. MICCAI 1999, Lecture Notes in Computer Science, Springer-Verlag (1999) 1679:798-808; and Masamune K, Patriciu A, Stoianovici D, Susil R, Taylor R H, Fichtanger G, Kavoussi L R, Anderson J, Sakuma I, Dom T: Development-of CT-PAKY frame system—CT image guided Needle puncturing manipulator and a single slice registration for urological surgery, Proc. 8th annual meeting of JSCAS, Kyoto 1999:89-90. These methods present an advantage of providing the registration data from a single image slice. In addition the methods are not restricted to the use of CTF. However, the registration frame of these methods are cumbersome in the confined gantry space, and its initial positioning with respect to the CT active field imposed stringent constraints for interventional use.

Thus, there is a need for new and improved image based target guiding systems and methods that take advantage of commonly available imaging technology and solve problems with the prior art.

SUMMARY OF THE INVENTION

The proposed method is significantly different from the prior art in that it is not an image-based registration method. The method of the present invention requires no additional hardware and is not limited-to the use of CTF scanners. The present invention is based on a laser-based registration principle and ensures zero radiation exposure for both the patient and personnel.

According to an embodiment of the present invention, a CT-robot registration system and method are provided that utilize laser markers of a CT scanner. Registration maybe used with traditional (non-CTF) scanners and does not require additional registration devices. Instead, the instrument (needle) can be used as a registration marker.

According to the present invention, needle access can be performed in an oblique direction, for which the skin entry point and the target are located in different CT slices. This is a significant improvement over prior art manual methods, in which the needle is restricted to the fluoro-image of the CTF scanner.

The present invention provides null radiation exposure for a radiologist controlling the procedure from the control room and minimizes the exposure to the patient. Therefore, the number of CT interventions a radiologist may safely perform during a given year is not restricted. Moreover, through the use of the disclosed process and system, the present invention reduces the variability in performing CT-guided percutaneous access.

According to an embodiment of the present invention, a laser based registration system is provided which includes a robot, a CT scanner, and a processor. The robot has an end-effector capable of holding an instrument, and is configured to orient the instrument about a point distal from the robot while maintaining one end of the instrument in contact with the point. The CT scanner includes laser markers and is configured to image an image slice. The processing unit is coupled with the robot and the CT scanner. The processing unit is also configured to control a movement of the robot, to determine the coordinate position of the robot, to receive imaging data from the CT scanner, and to calculate registration data by overlapping the instrument in image and robot coordinate systems.

According to another embodiment of the present invention, a method is provided for laser based instrument registration in a CT guided system. The system includes an operating table coupled with a robot holding an instrument, and CT scanner, wherein the CT scanner has first and second laser markers. The method includes steps of: moving the robot to align the instrument in a first position wherein a tip of the instrument is disposed within a first laser plane created by the first laser marker; moving the robot to align the instrument in a second position wherein the entire instrument is disposed within the first laser plane; obtaining coordinate data of the robot in the second position; obtaining image data of a first slice from the CT scanner; and calculating registration data based on the coordinate data and the image data.

BRIEF DESCRIPTION OF THE DRAWINGS

The objects and features of the invention will be more readily understood with reference to the following description and the attached drawings, wherein.

DETAILED DESCRIPTION OF THE PREFERRED EMBODIMENTS

Figure 1:
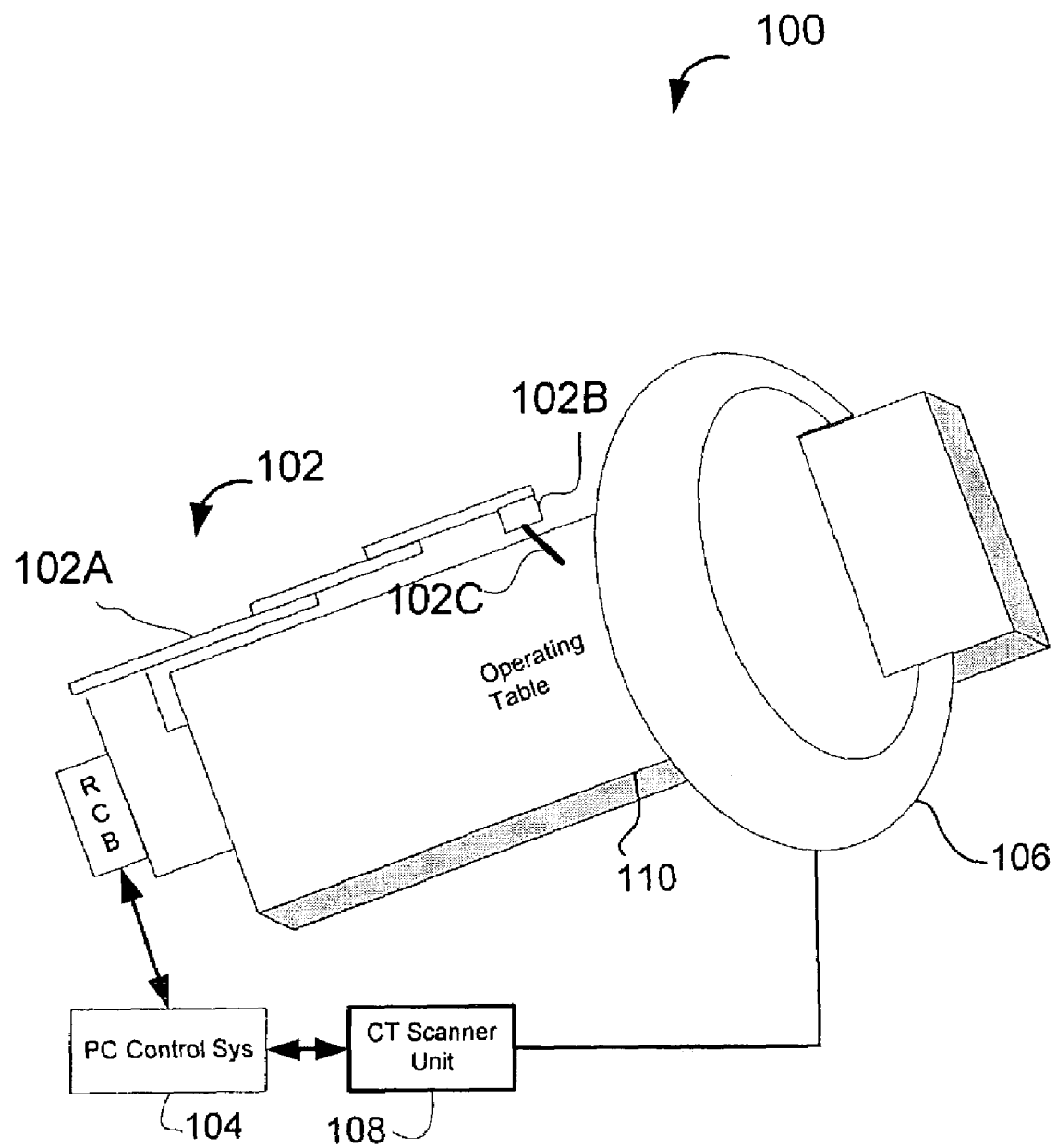
FIG. 1 is a block diagram of system for laser based CT and MR registration, according to an embodiment of the present invention.

Referring to FIG. 1, a system for laser based CT and MR registration comprises a CT scanner 106/108, a personal computer (PC) or processing unit 104, and a surgical robot 102. The surgical robot is preferably a remote center of motion (RCM) robot 102A coupled with an end-effector 102B, such as a percutaneous access of the kidney (PAKY) needle driver. By the method describe herein, the coordinate system of the robot 102 is matched with the coordinate system of CT scanner 106/108, i.e., registration is performed.

The CT scanner can be any conventional CT scanner equipped and configured to perform as described herein. As an example, the Siemens Somatom Plus Four™, manufactured by SIEMENS MEDICAL SYSTEMS is suitable for implementation of the present invention.

The RCM robot 102A can be a compact robot for surgical applications that is configured to implement a fulcrum point located distal to the mechanism. An exemplary RCM robot is described in co-owned, U.S. patent application Ser. No. 10/359,284, entitled, "REMOTE CENTER OF MOTION ROBOTIC SYSTEM AND METHOD" which was filed on Feb. 6, 2003 and issued as U.S. Pat. No. 7,021,173 on Apr. 4, 2006, and which is hereby incorporated by reference. The RCM robot 102 is configured to precisely orient a surgical instrument in space while maintaining the location of one of its points. Robot 102 is configured to rotate and extend as necessary to orient the surgical instrument. The kinematic architecture makes it proper for minimally invasive applications as well as trocar/needle 102C orientation in percutaneous procedures. RCM robot 102A can accommodate various end-effectors, such as a PAKY needle driver 102B.

The PAKY needle driver 102B is a radiolucent needle driver used to guide and actively drive a trocar needle 102C into the body for X-Ray guided percutaneous access procedures. The needle driver can be radiolucent, thus allowing unobstructed visualization of the anatomical target and radiological guidance of the needle. See Stoianovici D, Cadeddu J A, Demaree R D, Basile H A, Taylor R H, Whitcomb L F., Sharpe W, Kavoussi L R: An Efficient Needle Injection Technique and Radiological Guidance Method for Percutaneous Procedures, (1997), Lecture Notes in Computer Science, Springer-Verlag, 1205:295-298, which is incorporated herein by reference. The PAKY needle driver includes an electric motor that performs automated needle insertion. An exemplary PAKY needle driver is described in the following documents: Cadeddu J A, Stoianovici D, Chen R N, Moore R G, Kavoussi L R: Stereotactic mechanical percutaneous renal access, (1998), Journal of Endourology, 12:2:121-126; Patriciu A, Stoianovici D, Whitcomb L L, Jarrett T, Mazilu D, Stanimir A, lordachita I, Anderson J, Taylor R, Kavoussi-L R: Motion-Based Robotic Instrument Targeting Under C-Arm Fluoroscopy, (2000), MICCAI, Lecture Notes in Computer Science, Springer-Verlag, 1935;988-998; Stoianovici D, Cadeddu J A, Demaree R D, Basile H A, Taylor R H, Whitcomb L F., Sharpe W, Kavoussi L R: An Efficient Needle Injection Technique and Radiological Guidance Method for Percutaneous Procedures, (1997), Lecture Notes in Computer Science, Springer-Verlag, 1205:295-298; Stoianovici D, Whitcomb L L, Anderson J H, Taylor R H, Kavoussi L R: A Modular. Surgical Robotic System for Image Guided Percutaneous Procedures, (1998) Lecture Notes in Computer Science, Springer-Verlag, 1496:404-4.10, which are hereby incorporated by reference.

The PC 104 can be any commercially available computer processing unit or personal computer, which is configured with a motion control card, or similar device for robot control, and to acquire CT images in compliance with the well-known DICOM standard (Digital Images in Communications in Medicine) through a network connection (DICOM version 3.x provides standards and protocols for networked operation, see www.nema.org). Accordingly, CT images may be displayed on a display of PC 104 and robot 102 may be controlled by PC 104, via a client interface. PC 104 is also configured to perform the registration processes of the preset invention as further described in detail below.

Laser markers commonly available on a CT scanner can be used to perform robot registration, through needle alignment processes. A target is chosen in the image slice displayed on the monitor of PC 104, and the robot 102 automatically aligns and delivers the needle 102C. One having ordinary skill in the art will understand that many software and hardware mechanisms may be implemented to insure the safety of the procedure.

In the current setting, the PAKY-RCM robot is preferably used to orient a needle while maintaining its initial tip location and to perform the insertion of the needle. Two degrees of freedom (DOF) are used for needle alignment and one translational DOF is used for needle insertion. For safety, the orientation and insertion stages may be independently enabled/disabled by hardware means.

The robot 102 can be fixed into a passive arm, which can be attached over the CT table 110, such as by mounting on a bridge fixture 112. The passive arm allows for the support of the robot 102 in close proximity of the targeted organ so that the tip of the needle is located at the desired skin entry point. In this setting only two rotations and one translation are required for accessing any nearby target.

Figure 2:
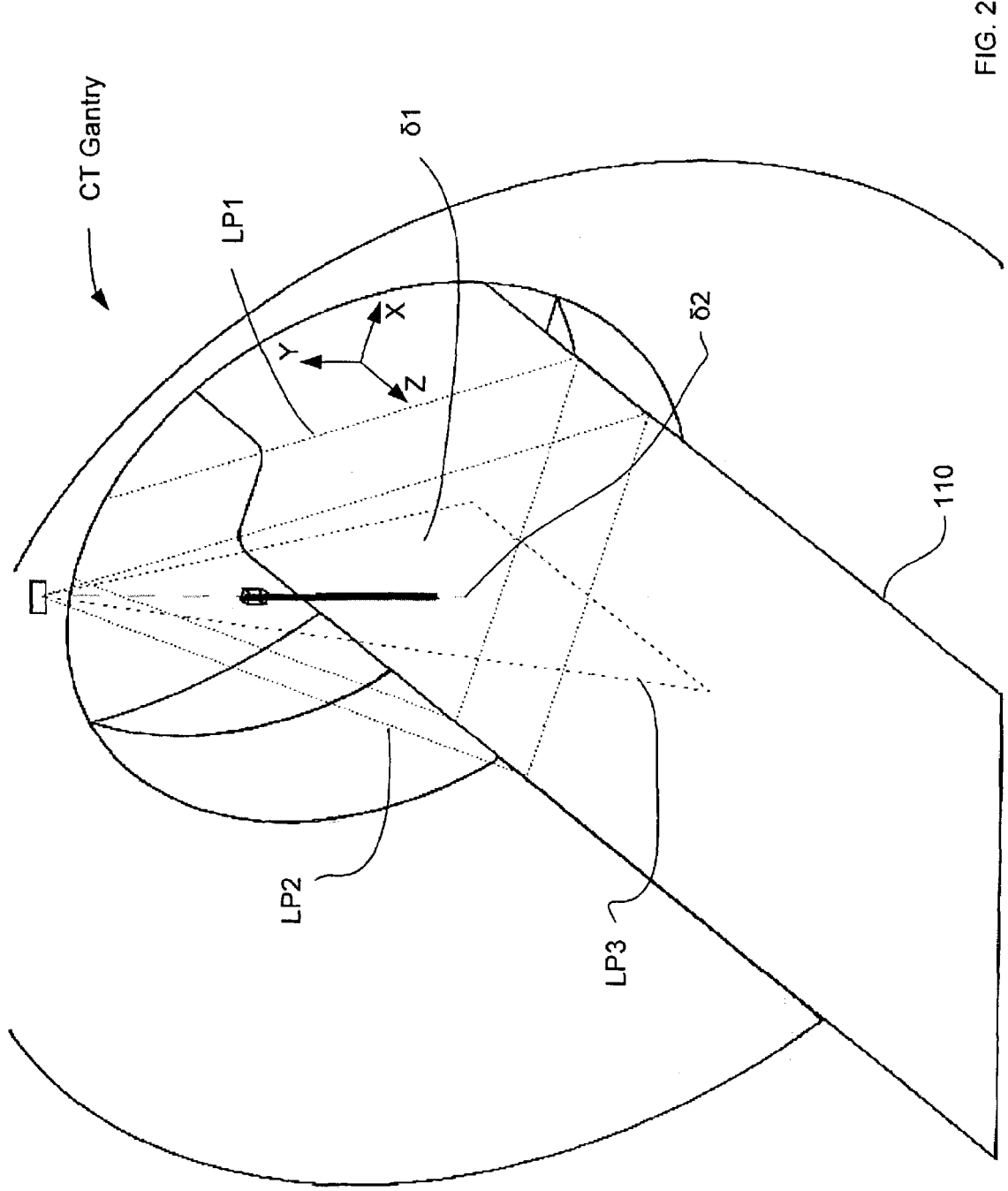
FIG. 2 is a diagram of the CT scanning and laser planes, according to an embodiment of the present invention.

FIG. 2 is a diagram showing an exemplary CT and MR scanner equipped with three laser markers. Laser Plane 1 (LP 1) coincides with the current CT image plane. Laser Plane 2

(LP2) is parallel with LP1 and positioned at the distance $Z_{12}$ along the Z-axis of the CT image space. Laser Plane 3 (LP3) is perpendicular to LP1 and LP2 and defines the YOZ plane of the CT image space. The intersection of the LP1 and LP3 planes defines the vertical direction $\delta 2$ in the CT image space.

The registration process of the present invention is based on the alignment of the instrument (e.g., needle) with the vertical direction $\delta_2$. This alignment can be achieved by simultaneously aligning the needle in the LP2 and LP3 laser planes. The central and vertical direction of the current CT image $\delta_1$ can be obtained by a simple $Z_{12}$ translation, by moving the CT table 110.

This alignment with the laser planes provides a four DOF registration. The remaining DOF, specifically the Y position of the needle tip, is unknown and remains to be determined from the CT image acquired for target specification.

According to the present invention, a combined laser-based registration process is described next with reference to FIGS. 2 and 3. The registration process involves two main steps, as follows:

Step 1: Define the current image plane (LP1) in the robot coordinate system by using the laser alignment process. Using the passive arm, RCM robot 102 is positioned so that the tip of the needle is located at the desired skin entry point. The CT table 110, together with the robot 102, is then moved until the tip of the needle is highlighted by the laser that lights LP1 (LP2 and a translation could also be used).

Figure 3:
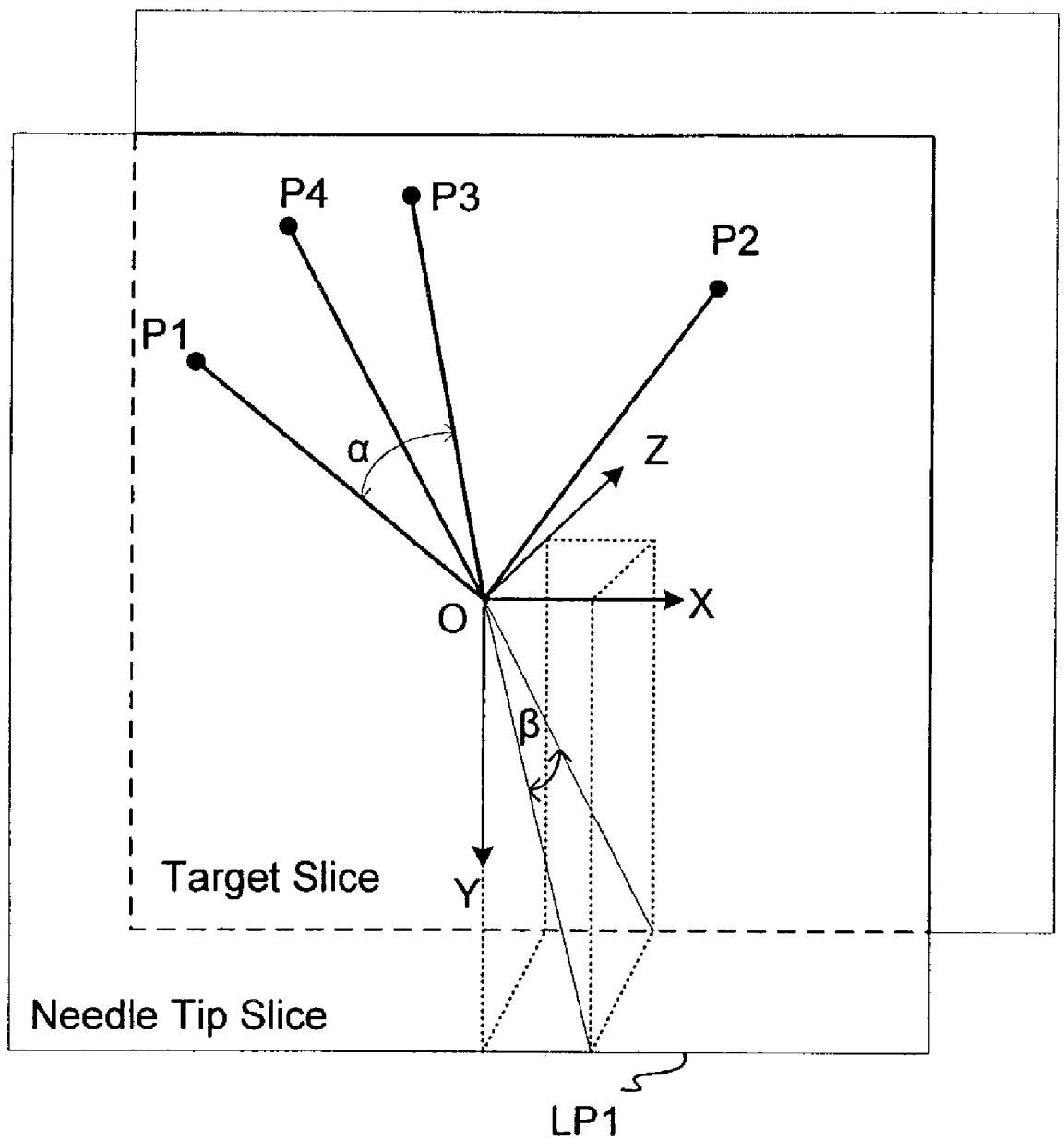
FIG. 3 is a diagram of instrument positions in two CT image slices, according to an embodiment of the present invention.

FIG. 3 shows several consecutive needle positions: positions $P_1O$, $P_2O$, $P_3O$, $P_4O$, with the needle point O being located in the image and laser plane LP1. The robot is moved under joystick control while observing the laser projection on the needle so that the needle head is aligned with the laser. During this motion, the RCM robot 102 insures that the needle tip remains in LP1. In the $P_1O$ position, the laser shines over its entire barrel of the needle.

According to the present invention, the needle may be set and inspected by direct observation. However, an automated method could be implemented.

The needle $P_1O$ is located in the current image and in laser plane LP1. PC 104 acquires the needle orientation by recording the joint coordinates of robot 102.

The process of needle alignment in the laser plane LP1 is then repeated for a different orientation of the needle $P_2O$. Joint coordinates are acquired at this position and geometric calculations are employed to define the $P_1OP_2$ plane in the robot coordinate system. The current image plane is defined in robot space, thus providing the first 2 DOF for the registration process. At this stage the robot may be restricted to move in the LP1 image plane. Thus, the needle may be remotely manipulated in the image space, in a similar way that radiologists presently perform CTF manual interventions.

Step 2: The remaining registration data is image-based and uses the image acquired for entry-point/target specification. An image is acquired at the same $P_1O$ orientation of the needle. The combined registration data is then calculated by overlapping the needle $P_1O$ in the image and robot spaces, providing the complete registration data, which will be used for orienting the needle towards the specified target.

An image slice is acquired through the needle-tip and through the desired target (needle tip slice and target slice in FIG. 3). In the case that the needle tip and the target are located in the same image plane, only one acquisition is required. The images are preferably acquired in DICOM format and displayed on the PC monitor. The radiologist can select the target by appropriate means in the computer interface, such as by using a computer mouse.

The transversal targeting angle $\alpha$ is determined by using simple geometric relations in the target slice image. The longitudinal targeting angle $\beta$ is then calculated by using the distance between the two slices retrieved from the DICOM images.

Under the control of the radiologist the robot automatically orients the needle at the position $P_4$ specified by the angles $\alpha$ and $\beta$ through the intermediary (in plane) position P3 (given by $\alpha$). In the particular case that the target and skin entry point are located in the same slice, all calculations are performed on the same image and $\beta=0$. The needle depth of insertion is calculated by using the image of the target and needle tip in the two slices.

Further explanation of the above-described process is as follows: Let FR be the robot coordinate frame and CTR be the CT coordinate frame. The RCM robot is kinematically equivalent with a sequence of two rotations, a rotation about the z-axis followed by a rotation about the y-axis, the needle being initially aligned with the y-axis. The registration process can be mathematically described as follows:

Step 1: The position of the needle in position $P_1O$ is:

$$\vec{v}_1 = R_z(\alpha_1)R_x(\beta_1)\begin{pmatrix}0\\1\\0\end{pmatrix}$$

where:

$\alpha_1$—joint angle for RCM axis 0 in $P_1O$ position;
$\beta_1$—joint angle for RCM axis 0 in $P_1O$ position.

The position of the needle in position $P_2O$ is:

$$\vec{v}_2 = R_z(\alpha_2)R_x(\beta_2)\begin{pmatrix}0\\1\\0\end{pmatrix}$$

where:

$\alpha_2$—joint angle for RCM axis 0 in $P_1O$ position;
$\beta_2$—joint angle for RCM axis 0 in $P_1O$ position.

Then, the image plane in robot space is defined as a plane that passes through the origin of the robot coordinate space (CS) and is orthogonal to the vector defined by:

$$\vec{n}_z = \frac{\vec{v}_2 \times \vec{v}_1}{\|\vec{v}_2 \times \vec{v}_1\|_2}$$

where x is the cross product of two vectors and $$\left\|\begin{pmatrix}a\\b\\c\end{pmatrix}\right\|_2 = \sqrt{a^2 + b^2 + c^2}.$$

Also, $\vec{n}_z$ defines the direction of the $\vec{z}$ axis of the image space in robot coordinates space.

Step 2: an image is acquired with the needle in position $P_1O$. The needle is identified in this image. From this image we can compute:

The position of the tip of the needle in image coordinates $$\vec{t}_i = \begin{pmatrix} t_x \\ t_y \\ t_z \end{pmatrix}.$$

Since the origin of the robot CS is at the tip of the needle $\vec{t}_i$ will represent the translation from the image CS to the robot CS. The orientation of the x-axis of the image CS with respect to $P_1O$, specifically the angle $\phi$ with which we need to rotate $P_1O$ to obtain $\vec{x}$. Thus, the position of the x-axis of the image CS in robot CS ($\vec{n}_x$) is obtained rotating $\vec{v}_1$ around $\vec{n}_z$ with $\phi$ degrees.

The y-axis of the image CS in robot CS is then:

$$\vec{n}_y = \vec{n}_z \times \vec{n}_x;$$

with $\vec{n}_x$, $\vec{n}_y$, $\vec{n}_z$ and $\vec{t}_i$ the position of a point $\vec{p}$ defined in image CS will be in robot $$CS: \vec{p}_r = (\vec{n}_x \vec{n}_y \vec{n}_z)(\vec{p} - \vec{t}_i).$$

Thus, provided is a novel system and method for performing instrument registration.

Preliminary accuracy testing was performed in-vitro using 1 mm diameter metallic balls. The target was placed in the same image plane with the needle tip and also in different planes. The targeting error achieved over fifty experiments was less than 1 mm in plane and 1.5 mm for out of plane targets. With these satisfactory results, the extensive clinical experience with the PAKY-RCM robot in percutaneous renal access under C-Arm guidance, and the safety of the PAKY-RCM robot rendered by its decoupled needle orientation and insertion capability, the clinical application was tried. For verifying needle-targeting accuracy-before needle insertion, in the studies a CTF scanner was used. In addition, in all clinical applications, several algorithm-testing steps were performed insuring the functionality of the algorithm in successive phases.

The table was then moved, together with the robot, so that the needle tip was located in the laser plane. Using the joystick the robot was moved in two different position ($P_1$ and $P_2$) located in the laser plane, these directions were acquired by the PC, and used for computing the position of the CT-slice in the robot space. For testing, the control was then transferred to the computer and the robot was moved back and forth in the laser plane to insure its correct determination. This was visually acknowledged by observing the laser projection on the barrel of the needle during the in-plane motion. In all needle orientation phases the tip of the needle was located at the skin site and needle insertion was hardware disabled.

A scan was then taken with the needle at the first position (P1). The image was transferred to the PC, the needle tip was identified in the image, and the orientation of the needle in image was determined, finalizing the registration process. To verify the registration result, the needle was moved to the vertical in-slice position and a new image slice was acquired for confirmation.

A second scan was acquired. This image was also transferred to the PC and the radiologist indicated the lesion on the PC monitor. The program computed the needle targeting angles ($\alpha$ and $\beta$) and the required depth of insertion.

With needle insertion disabled, under the command of the radiologist, the robot oriented the needle towards the target. During this motion the needle was entirely outside the body only its tip being located at the skin level. Needle orientation accuracy was then verified by the radiologist under fluoro imaging.

Finally, the RCM orientation stage was disabled and the PAKY needle driver was enabled on the hardware. At the radiologist's command the needle was inserted under direct fluoro supervision.

The remaining steps of the procedure were then performed as usual.

Although the invention has been described based upon these preferred embodiments, it would be apparent to those of skilled in the art that certain modifications, variations, and alternative constructions would be apparent, while remaining within the spirit and scope of the invention. In order to determine the metes and bounds of the invention, therefore, reference should be made to the appended claims.

Note that a fourth laser could be used for providing a five DOF laser registration by marking a horizontal plane. CT scanners, however, are not normally equipped with such a fourth laser marker.

Subsets of this methodology may also be implemented for particular applications and robot kinematic schemes requiring reduced DOF registration.

We claim:

1. A laser-based registration system, comprising:
   a robot having an end-effector capable of holding an instrument, said robot configured to orient said instrument about a point distal from said robot while maintaining one end of said instrument in contact with said point;
   a CT scanner having laser markers and configured to image an image slice; and
   a processing unit coupled with said robot and said CT scanner, said processing unit configured to control a movement of said robot, to determine the coordinate position of said robot, to receive imaging data from said CT scanner, and to calculate registration data by overlapping said instrument in image and robot coordinate systems.

2. The system according to claim 1, wherein said CT scanner includes three laser markers for creating three laser planes, respectively, a first and second laser plane being parallel to each other and being perpendicular to a third laser plane.

3. The system according to claim 1, wherein said registration data is based upon imaging data collected for two positions of said instrument, as placed by said robot.

4. The system according to claim 2, wherein said registration data is based upon imaging data collected for two positions of said instrument, as placed by said robot.

5. The system according to claim 1, wherein said processing unit includes an interface unit for allowing manual manipulation of said robot.

6. The system according to claim 4, wherein said processing unit includes an interface unit for allowing manual manipulation of said robot.

7. The system according to claim 2, wherein said first laser plane is coincident with a current CT image plane of said scanner.

8. The system according to claim 4, wherein said first laser plane is coincident with a current CT image plane of said scanner.

9. The system according to claim 4, wherein said registration data is calculated further based upon first coordinate data of said robot when said instrument is disposed entirely in said first laser plane in a first position.

10. The system according to claim 8, wherein said registration data is calculated further based upon second coordinate data of said robot when said instrument is disposed entirely in said first laser plane in a second position.

11. The system according to claim 9, wherein said registration data is calculated further based upon first image data of said robot when said instrument is disposed entirely in said first laser plane in said first position.

12. The system according to claim 10, wherein said registration data is calculated further based upon second image data of said robot when said instrument is disposed entirely in said first laser plane in said second position.

13. A method for laser-based instrument registration in a CT-guided system including an operating table coupled with a robot holding an instrument, and CT scanner, said CT scanner having first and second laser markers, said method comprising steps of:
 moving said robot to align said instrument in a first position wherein said instrument and a tip of said instrument are disposed entirely within a first laser plane created by said first laser marker when in the first position, wherein said first lser plane is coincident with a CT image plane of said CT scanner;
 obtaining coordinate date of said robot in said first position;
 moving said robot to align said instrument in a second position wherein said entire instrument is disposed within said first laser plane;
 obtaining coordinate data of said robot in said second position;
 obtaining image data of a first slice from said CT scanner; and
 calculating registration data based on said coordinate data and said image data.

14. The method according to claim 13, wherein said step of moving said robot to align said instrument in a first position alignment includes moving said robot to align said instrument in said first position and moving said table until said instrument is disposed within a first laser plane created by said first laser marker.

15. The method according to claim 14, further including steps of:
 moving said robot to align said instrument in a third position wherein a tip of said instrument is disposed within a first laser plane created by said first laser marker;
 moving said robot to align said instrument in a fourth position wherein said entire instrument is disposed within said first laser plane;
 obtaining coordinate data of said robot in said fourth position;
 obtaining image data of a second slice from said CT scanner; and
 wherein said step of calculating registration data is based on said coordinate data for said second and fourth position and said image data of said first and second slice.

16. The method according to claim 15, further comprising a step of calculating geometric information about a plane created by said second and fourth positions to define a current image plane in robot space.

17. The method according to claim 13, wherein said step of calculating registration data includes overlapping coordinate data of said robot in said second position with image data about said instrument in said second position.

18. A laser-based registration system, comprising:
 a robot means for holding and orienting an instrument about a point distal from said robot means and while maintaining one end of said instrument in contact with said point;
 a CT scanner means for providing laser markers and imaging an image slice; and
 a processing means for controlling a movement of said robot means, for determining the coordinate position of said robot means, and for receiving imaging data from said CT scanner means and calculating registration data by overlapping said instrument into image and robot coordinate systems.

19. The system according to claim 18, wherein said CT scanner means includes three laser markers for creating three laser planes, respectively, a first and second laser plane being parallel to each other and being perpendicular to a third laser plane.

20. The system according to claim 18, wherein said registration data is based upon imaging data collected for two movements of said instrument by said robot means.

21. The system according to claim 19, wherein said registration data is based upon imaging data collected for two positions of said instrument, as placed by said robot means.

22. The system according to claim 18, wherein said processing means includes an interface means for allowing manual manipulation of said robot means.

23. The system according to claim 21, wherein said processing means includes an interface means for allowing manual manipulation of said robot means.

24. The system according to claim 19, wherein said first laser plane is coincident with a current CT image plane of said CT scanner means.

25. The system according to claim 21 wherein said first laser plane is coincident with a current CT image plane of said CT scanner means.

26. The system according to claim 21, wherein said registration data is calculated further based upon first coordinate data of said robot means when said instrument is disposed entirely in said first laser plane in a first position.

27. The system according to claim 25, wherein said registration data is calculated further based upon second coordinate data of said robot means when said instrument is disposed entirely in said first laser plane in a second position.

28. The system according to claim 26, wherein said registration data is calculated further based upon first image data of said robot means when said instrument is disposed entirely in said first laser plane in said first position.

29. The system according to claim 27, wherein said registration data is calculated further based upon second image data of said robot means when said instrument is disposed entirely in said first laser plane in said second position.

* * * * *